(12) United States Patent
Bacon

(10) Patent No.: US 10,586,616 B2
(45) Date of Patent: Mar. 10, 2020

(54) SYSTEMS AND METHODS FOR GENERATING SUBSETS OF ELECTRONIC HEALTHCARE-RELATED DOCUMENTS

(71) Applicant: 3M INNOVATIVE PROPERTIES COMPANY, St. Paul, MN (US)

(72) Inventor: David R. Bacon, Sandy, UT (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 16/290,533

(22) Filed: Mar. 1, 2019

(65) Prior Publication Data

US 2019/0198141 A1  Jun. 27, 2019

Related U.S. Application Data

(63) Continuation-in-part of application No. 12/474,015, filed on May 28, 2009, now abandoned.

(51) Int. Cl.
| | | |
|---|---|---|
| *G06Q 50/00* | (2012.01) | |
| *G16H 10/60* | (2018.01) | |
| *G06Q 10/06* | (2012.01) | |
| *G06Q 10/08* | (2012.01) | |
| *G06Q 10/10* | (2012.01) | |

(52) U.S. Cl.
CPC ............ *G16H 10/60* (2018.01); *G06Q 10/06* (2013.01); *G06Q 10/0875* (2013.01); *G06Q 10/10* (2013.01)

(58) Field of Classification Search
USPC ........................................................ 705/2–4
See application file for complete search history.

(56) References Cited

U.S. PATENT DOCUMENTS

| | | | |
|---|---|---|---|
| 6,055,494 A | 4/2000 | Friedman | |
| 6,182,029 B1 * | 1/2001 | Friedman | ............ G06F 17/2705 704/9 |
| 6,292,771 B1 | 9/2001 | Haug et al. | |
| 6,556,964 B2 | 4/2003 | Haug et al. | |
| 6,915,254 B1 | 7/2005 | Heinze et al. | |
| 7,233,938 B2 * | 6/2007 | Carus | ................... G06Q 50/22 705/2 |
| 7,610,192 B1 * | 10/2009 | Jamieson | ............ G06F 17/2229 704/9 |
| 2004/0073458 A1 | 4/2004 | Jensen | |
| 2004/0172297 A1 | 9/2004 | Rao et al. | |
| 2004/0220831 A1 | 11/2004 | Fabricant | |
| 2004/0243545 A1 | 12/2004 | Boone et al. | |
| 2005/0120020 A1 | 6/2005 | Carus et al. | |
| 2005/0137910 A1 | 6/2005 | Rao et al. | |

(Continued)

FOREIGN PATENT DOCUMENTS

WO  WO 2007/136852 A2  11/2007

OTHER PUBLICATIONS

Adams, Diane L., Helen Norman, and Valentine J. Burroughs. "Addressing medical coding and billing part II: a strategy for achieving compliance. A risk management approach for reducing coding and billing errors." Journal of the National Medical Association 94.6 (2002): 430.*

*Primary Examiner* — Mark Holcomb
(74) *Attorney, Agent, or Firm* — Jonathan L. Tolstedt

(57) ABSTRACT

Systems and methods for displaying subsets of electronic documents generated in association with a patient's encounter with a healthcare organization.

22 Claims, 10 Drawing Sheets

(56) References Cited

U.S. PATENT DOCUMENTS

| | | | |
|---|---|---|---|
| 2005/0240439 A1 | 10/2005 | Covit et al. | |
| 2006/0095294 A1 | 5/2006 | Compton et al. | |
| 2006/0106795 A1 | 5/2006 | Compton et al. | |
| 2006/0129435 A1* | 6/2006 | Smitherman | G06F 19/324 |
| | | | 705/3 |
| 2007/0233660 A1 | 10/2007 | Rogers | |
| 2008/0004505 A1* | 1/2008 | Kapit | G16H 15/00 |
| | | | 600/300 |
| 2008/0288292 A1* | 11/2008 | Bi | G06Q 50/24 |
| | | | 705/3 |

* cited by examiner

Fig. 5

Patient Visit ID:
12345678

© Codefinder Status: Patient Code Summary

Search

Views
- Coder View
- Cross Reference
- Operative Report
- Discharge Summary
- History And Physical
- Physician Progress Notes ▽ Coder View □ Discharge Summary — 510

PHYSICIAN/SURGEON: Myron P. Gynsburg, MD — 540

DATE OF DISCHARGE: 10/14/2004 — 545

ADMITTING DIAGNOSES: (1) Recalcitrant postmenopausal bleeding (on hormonal replacement therapy); (2) leiomyomata uteri.

FINAL DIAGNOSES: (1) Cellular leiomyoma — 572 with focal atypia; (2) leiomyomata uteri; (3) adenomyosis; superficial; (4) postmenopausal bleeding, recalcitrant (or hormonal replacement therapy). — 550   560   570

□ Operative Report — 520

SURGEON: Myron P. Gynsburg, MD

DATE OF PROCEDURE: 10/11/2004

OPERATION: 1. Total abdominal hysterectomy — 580   2. Bilateral salpingo-oophorectomy — 585

□ Discharge Summary — 530

HISTORY OF PRESENT ILLNESS:
The patient is a 55-year-old, G1/P1, white female, six years postmenopausal. She has been known to have uterine fibroids for 20 years. Her uterus has remained about 10-week size over the past decade, and the fibroids have been relatively asymptomatic. She began cyclic hormonal replacement therapy in 1998 and did well with that for two years. In early 2000, she complained of continued cyclic bleeding and was switched to continuous therapy with Premarin 0.625 mg daily and Provera 5 mg daily. Thereafter, she was bothered by intermittent light bleeding for six months. Endometrial biopsy performed in August 2000 was benign. She was reassured by these findings. In March 2001, the Provera dosage was decreased to 2.5 mg daily, and she underwent hysteroscopy and D&C. The former suggested small, flat, almost flush fundal submucosal fibroids, and the surgical specimen yielded "scant fragments of inactive / atrophic endometrium." Two months later, because of continued bleeding, the estrogen dosage was increased to 0.9 mg Premarin daily. The problem continues, and she requests definitive resolution therof.

Local Intranet  100%

Fig. 6

Patient Visit ID: 12345678

Codefinder : Diagnosis

[LEIOMYOMA] — 610

Views
- Coder View
- Operative Report
- Discharge Summary
- History And Physical
- Physician Progress Notes Image documents are not included in cross reference or search results.

▽ ▷ Cross Reference-leiomyoma

Operative Report

PREOPERATIVE DIAGNOSIS:
▷ Leiomyomata uteri 2 — 612

OPERATIVE FINDINGS: — 612
▷ There was a prominent 4- to 5-cm diameter subserosal leiomyoma coming off the right fundal portion of the uterus.
▷ There was a smaller, 7- to 8-mm submucosal leiomyoma — 612 that was almost flush with the endometrial cavity and not protruding significantly therein.

Discharge Summary

ADMITTING DIAGNOGSIS:
▷ (1) Recalcitrant postmenopausal bleeding (on hormonal replacement therapy); 2) leiomyomata uteri.

HOSPITAL COURSE:
▷ At surgery the uterus was found to be approximately 8-week gestational size with a prominent 4- to 5-cm subserosal leiomyoma of the right fundus and a 7- to 8-cm submucosal leiomyoma, which was almost flush with the endometrial cavity in the fundal area.

LABORATORY DATA:
▷ The evaluation of the surgical specimen by the Department of Surgical Pathology demonstrated a uterus that weighed 170 g. Benign-appearing multple leiomyomata were identified, as was superficial adenomyosis.
▷ Of the most significance is the fact that one of the leiomyomata was described as a "cellular leiomyoma with focal atypia.

Fig. 8

Views
- ☐ Coder View
- ☐ Operative Report
- ☐ Discharge Summary
- ☐ History And Physical
- ☐ Physician Progress Notes Image documents (📄) are not included in cross reference or search results.

Patient Visit ID: 12345678

Codefinder: Diagnosis sub:
- subcutaneous (1)
- subcuticular (1)
- submucosal (3)  } — 810
- subserosal (2)
- subumbilical (1)

▸ Leiomyomata uteri 2

OPERATIVE FINDINGS:
▸ There was a prominent 4- to 5-cm diameter subserosal leiomyoma coming off the right fundal portion of the uterus.
▸ There was a smaller, 7- to 8-mm submucosal leiomyoma that was almost flush with the endometrial cavity and not protruding significantly therein.

⊟ Discharge Summary

ADMITTING DIAGNOSIS:
▸ (1) Recalcitrant postmenopausal bleeding (on hormonal replacement therapy); 2) leiomyomata uteri.

HOSPITAL COURSE:
▸ At surgery the uterus was found to be approximately 8-week gestational size with a prominent 4- to 5-cm subserosal leiomyoma of the right fundus and a 7- to 8-cm submucosal leiomyoma, which was almost flush with the endometrial cavity in the fundal area.

LABORATORY DATA:
▸ The evaluation of the surgical specimen by the Department of Surgical Pathology demonstrated a uterus that weighed 170 g. Benign-appearing multiple leiomyomata were identified, as was superficial adenomyosis.
▸ Of the most significance is the fact that one of the leiomyomata was described as a "cellular leiomyoma with focal atypia.

610

SYSTEMS AND METHODS FOR GENERATING SUBSETS OF ELECTRONIC HEALTHCARE-RELATED DOCUMENTS

BACKGROUND

In order for healthcare organizations to receive remuneration from payment organizations (such as insurers or the government) for services provided to a patient, payment requests need be submitted to the payment organizations. These payment requests describe services provided to the patient via a set of standardized codes. The payment organization reviews the codes and then makes a payment.

To represent the healthcare organization's services via codes, a medical coder reviews documents generated in association with the healthcare organization's encounter with the patient. Often these documents are generated by doctors or other healthcare professionals that interact with and provide services to the patient. Examples of such documents include a discharge summary or an operative report. Complex patient encounters (such as a difficult surgery) might yield dozens of documents, each of which will be reviewed by the medical coder. Many of these documents do not adhere to particular formatting. Some of the documents are hand written or scanned.

Medical coders review these documents and identify billable aspects of the patient encounter, and then associate these billable aspects with codes. This review process, which includes reading, navigating, and assessing documentation, is cumbersome, sometimes requiring up to 70% of a medical coder's time.

SUMMARY

Systems and methods for creating one or more subsets of electronic documents associated with a patient's encounter with a healthcare organization. In various embodiments described herein, these subsets may contain information of particular relevance to a coders' job of sifting through the electronic documents and associating codes with billable aspects of the patient's encounter. In various embodiments, these subsets allow a coder to concentrate his or her time and effort on the most relevant portions of electronic documents, which may save the coder time, and thus the coder's employer money.

In one embodiment, a computer-implemented method is described, the method comprising: receiving a plurality of electronic documents associated with a patient's encounter with a healthcare organization; receiving a set of rules from a rules database, the rules defining, for given types of electronic documents, portions of the electronic documents that may be of interest to a coder; applying the set of rules to the plurality of electronic documents to produce subsets of the electronic documents; and, generating in a user interface a display area that includes subsets of at least two of the electronic documents.

In another embodiment, a computer-readable medium is described, the computer readable medium containing instructions that when executed by a computer having a processor and memory cause the computer to: receive a plurality of electronic documents associated with a patient's encounter with a healthcare organization; receive a set of rules from a rules database, the rules defining, for given types of electronic documents, portions of the electronic documents that may be of interest to a coder; apply the set of rules to the plurality of electronic documents to produce subsets of the electronic documents; and, generate in a user interface a display area that includes subsets of at least one of the electronic documents.

In another embodiment, a system is described, the system comprising one or more microprocessors and memory which executes software to cause the system to: receive a plurality of electronic documents associated with a patient's encounter with a healthcare organization; receive a set of rules from a rules database, the rules defining, for given types of electronic documents, portions of the electronic documents that may be of interest to a coder; apply the set of rules to the plurality of electronic documents to produce subsets of the electronic documents; and, generate in a user interface a display area that includes subsets of at least one of the electronic documents.

BRIEF DESCRIPTION OF DRAWINGS

FIG. 5 is a screenshot from a user interface of the MDAE system.

FIG. 6 is a screenshot from a user interface of the MDAE system.

FIG. 8 is a screenshot from a user interface of the MDAE system.

DETAILED DESCRIPTION

Figure 1:
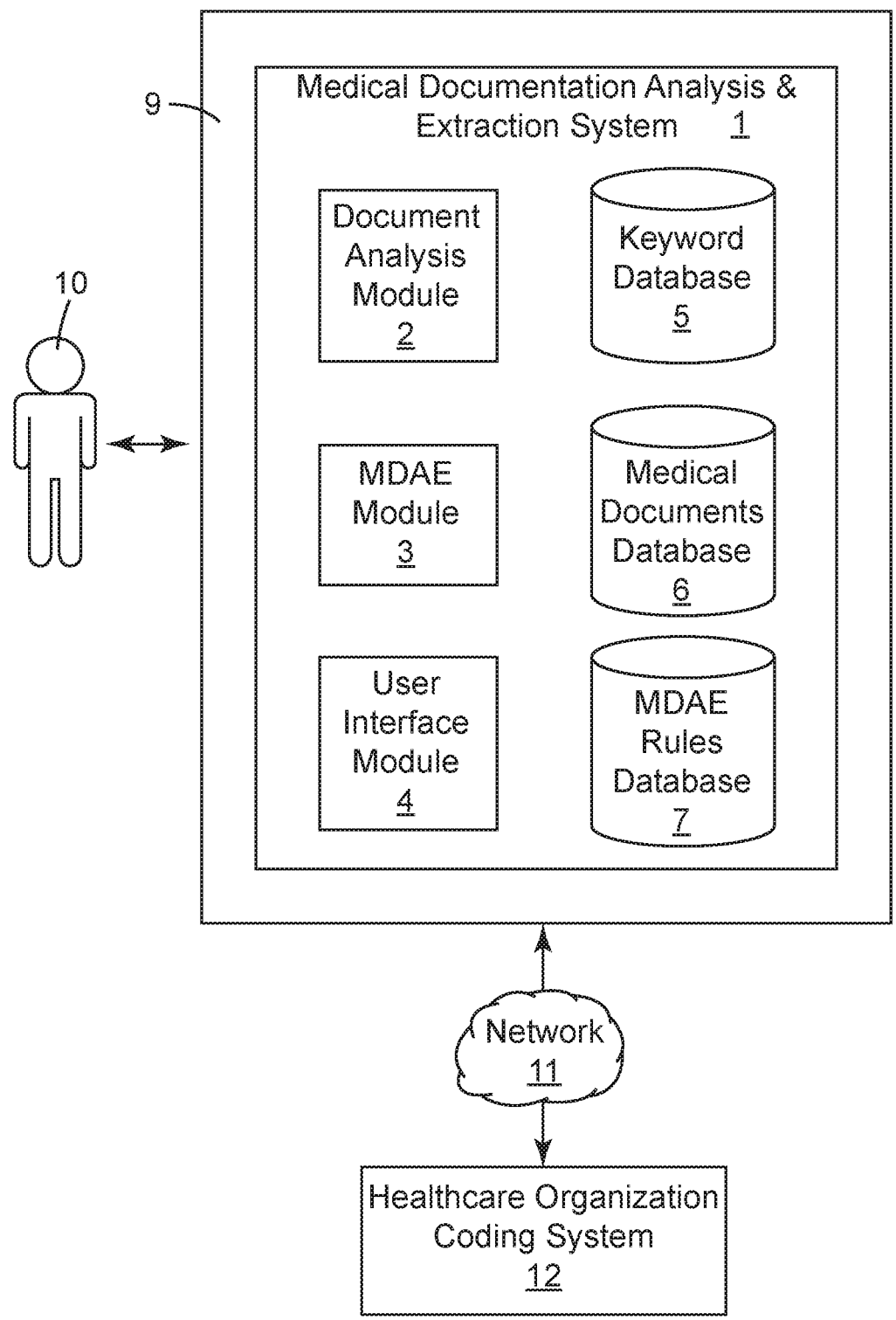
FIG. 1 is a diagram showing systems that might be used by a healthcare organization, including one embodiment of the Medical Documentation Analysis and Extraction (MDAE) system.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

A coding and reimbursement system is a computer software-based system used by a medical coder to describe a patient's encounter with a healthcare organization in a standardized manner. Coding and reimbursement systems utilize a defined set of codes, which associate procedures or diagnosis with particular alpha-numeric codes. The most important set of such codes, and the one most coding and reimbursement systems are based upon, is the International Classification of Diseases (ICD) published by the World Health Organization. The ICD uses six-character codes to classify diseases and a wide variety of signs, symptoms, abnormal findings, complaints, social circumstances and external causes of injury or disease. The ICD is updated periodically, the current version being referred to as ICD-9-CM. Modern versions of the ICD also include codes used to classify procedures.

The ICD is a hierarchy of diseases and procedures. For example, the ICD-9 code for pneumonia is 486; bacterial pneumonia (a type of pneumonia) has the code 482.9. Currently available coding and reimbursement systems take different approaches in how a coder navigates through the ICD hierarchy to arrive at a specific disease code. Some systems employ a code look-up approach whereby a coder identifies the diagnosis code, and is then presented with sub-code selections that are associated with the diagnosis. In the case of pneumonia, upon a coder selecting ICD code 486, he or she would be presented with the several more specific coding choices associated with pneumonia (for example, bacterial, aspiration, or anthrax). The coder would than choose the appropriate codes based on what is documented in the system.

Another approach to coding is termed the clinical approach, which involves asking questions that are related to ICD-defined diagnosis and procedures. The coder would initially identify pneumonia, just as with the code look-up approach mentioned above. Then, rather than being presented with sub-selections, the clinical approach would involve a computer system asking questions. For example, the computer system would ask the coder if the patient had bacterial, aspiration, inhalation or any other condition associated with pneumonia. If the coder selected bacterial, the system would ask the coder what the bacterial pneumonia was due to, and present possibilities like hemophilus influenza, mixed bacterial, or *streptococcus*. This approach helps the coder ensure that they are coding all associated conditions and procedures associated with the patients care.

FIG. 1 is a diagram showing representative systems that might be used by a healthcare organization. Healthcare organization coding system 12 may be one of several commercially available coding systems. One such coding system is that which is marketed by 3M Health Information Systems of Salt Lake City, Utah under the trade name "3M Coding & Reimbursement System". The healthcare organization coding system 12 facilitates the process of representing a patient's encounter with a healthcare organization via codes, which can then be submitted to a payment organization, such as an insurer or the government, for review and payment. Healthcare organization coding system 12 may have one or more interfaces to interact with a coder, such as coder 10. In the example shown in FIG. 1, this interface is the medical documentation analysis and extraction system ("MDAE system") 1, which will be described in greater detail below. However, instead of or in addition to the MDAE system, other interfaces could exist. For example, healthcare organization coding system 12 may provide a web-based interface where coder 10 can access and enter codes that define aspects of a patient's encounter with the healthcare organization. Alternatively, healthcare organization coding system 12 could provide its own graphical user interface. In various embodiments, the healthcare organization coding system may support a plurality of such interfaces.

Coder 10 is typically an individual employed by the healthcare organization to review medical documentation associated with a patient's encounter with the healthcare organization, and then represent billable aspects of the encounter in codes recognized by payment organizations. Payment organizations are typically insurers or government institutions. MDEA 1 provides an improved way for coder 10 to interact with healthcare organization coding system 12. Coder 10 uses a keyboard and other input devices (such as a pointing device such as a mouse or a touch screen) to interact with MDEA system 1.

MDEA system 1 is shown as software being executed on physical computer system 9. The software is contained on a computer-readable medium such as a hard drive, computer memory, a CD-ROM, a DVD, or any other computer-readable medium. Physical computer system 9 may be any computer having a processor and memory. In one embodiment, physical computer system 9 is a personal computer. In another embodiment it is a sever computer that interacts with coder 10 in a client/server type computing environment (this architecture is not depicted in FIG. 1). Though shown residing on one physical computing system 9, other embodiments may have various components of the MDAE system 1 operating on different, communicatively coupled computers. Physical computer system 9 includes an operating system (not shown in FIG. 1) to allocate processing, memory, network, and other computing resources to MDAE system 1. MDEA system 1 includes a number of functional and storage modules. The functionality of the functional modules will be described in greater detail later in this description. At a high level, however, MDAE module 3 controls the other MDAE modules, and controls functionality described herein not tied to any other module. MDAE module 3 facilitates retrieving medical documentation of various types from various databases associated with the healthcare organization. Medical documentation is placed in storage module medical documentation database 6. Medical documentation database 6, and other databases referred to herein, may be any type of data storage and retrieval system, such as flat files, an object-oriented database, or a relational database system.

With documents in the medical documents database 6, MDAE module 3 may invoke document analysis module 2. For a given patient's encounter with a healthcare organization, document analysis module 2 iterates through associated documentation in the medical documentation database 6. Document analysis module 2 has two principle objectives.

First, document analysis module 2 identifies portions of documents that have been pre-defined to be of particular relevance to coder 10. This pre-definition takes the form of rules stored in MDAE rules database 9, which are accessed by document analysis module 2. A rule might declare that medical documents having certain attributes are more (or less) relevant to coders than others. The rules might further declare that portions of documents having particular attributes are of higher relevance. In the end, application of the rules from MDAE rules database 7 yields data defining subsets of the medical documents.

Second, document analysis module 2 iterates through the subsets of documents and compares terms found in the medical documents to terms found in keyword database 5. Keyword database 5 is a database having keywords (including phrases) as well as other information specific to one or more ICD codes. For example, if a particular term is found, that term may be suggestive of a particular ICD code. This information is associated with the term. In one embodiment, this association is facilitated by creating a new version of the document in a markup language that allows for the imbedding of metadata with terms, such as HTML, or some variant of XML.

When the medical documentation has been analyzed by document analysis module 2, the document is passed by MDAE module 3 to user interface module 4, to display identified document subsets, with various visual indicia associated with identified terms. Additionally, functionality is provided such that, in one embodiment, upon coder 10 selecting the term (such as clicking it or visual indicia associated with it), the healthcare organization coding system 12 is invoked, and coder 10 is places as far into the coding hierarchy as is possible. This saves coder time, and reduces the chance of coder error because there are fewer selections that need to be made by the coder.

Figure 2:
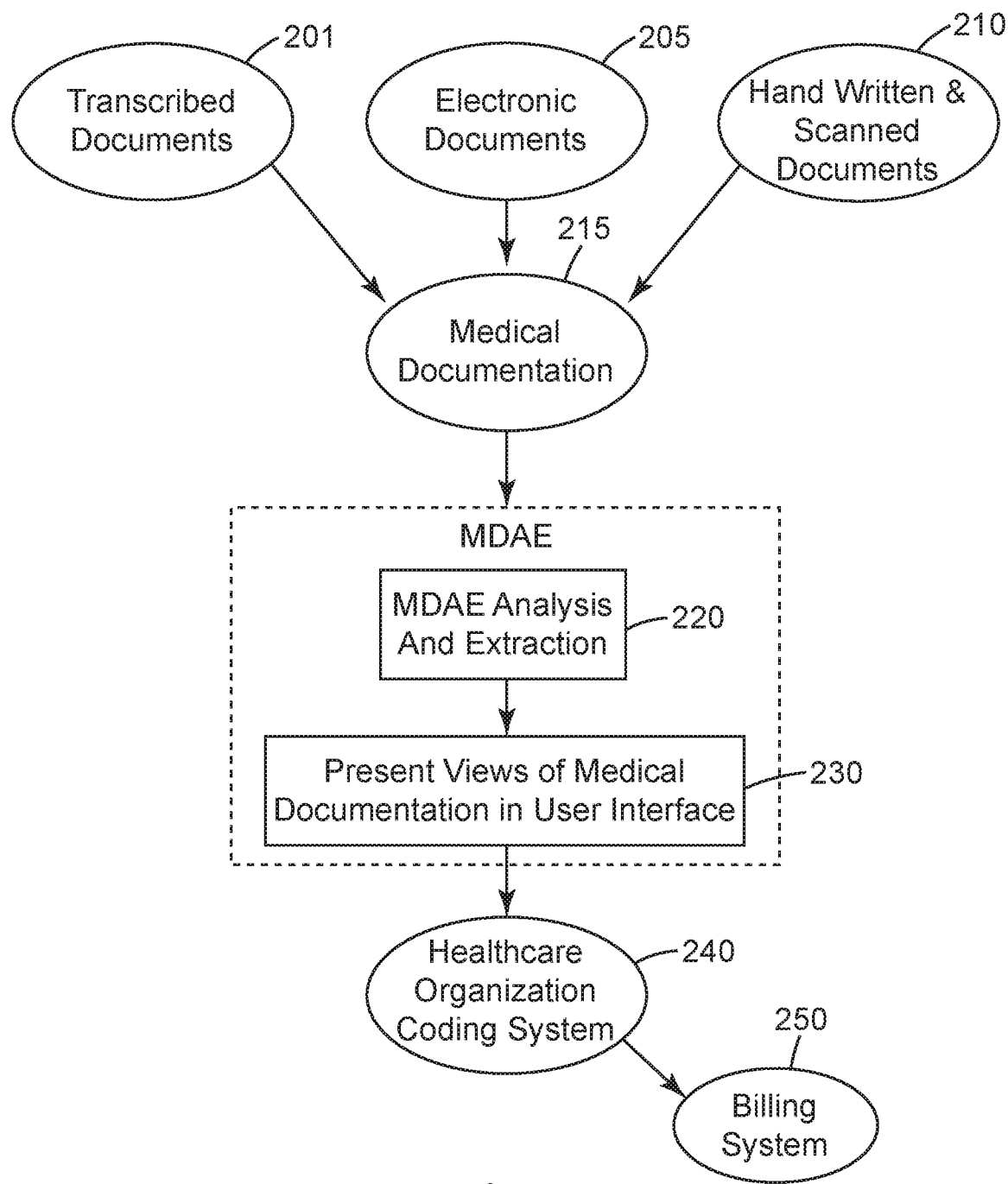
FIG. 2 is a high-level flowchart showing functionality of the MDAE system.

FIG. 2 is a high-level flowchart showing functionality of the MDAE system. Documents having information concerning a patient's interaction with a healthcare organization identified. These documents could take various forms. For example, they could be transcribed documents (201), electronic documents (205), or even handwritten and scanned documents (210). Collectively, these document sets comprise medical documentation 215 that could be relevant to coder 10 for coding billable aspects of the patient's interaction with the healthcare organization. Medical documentation 215 may include the patient's history and physical, physician and nursing progress notes, ancillary reports (laboratory, radiology, and so forth) and a discharge summary that describes the complete patient's stay. In an example later used in this description, medical documentation includes a discharge summary, emergency report and several consultation reports. It is not necessary for the medical documentation 215 to be located on a single place or on a single database system. As will be seen in subsequent discussion of the MDAE system, an initial procedure of the MDAE system is to retrieve medical documentation. This procedure may be customized to the environment in which the MDAE system is configured, and will often in practice mean retrieval from several different disparately located systems.

Once the MDAE system has access to medical documents 215, it proceeds with two high-level process steps. The first high-level process step comprises analysis and extraction (220). This will be discussed in further detail below, but generally comprises iterating through the medical documentation and identifying portions of the medical documents 215 that are relevant to coding, as well as, within those portions of the documents, terms relevant to coding. Once the analysis and extraction step is completed, the identified portions (and associated relevant terms) of the medical documents 215 are displayed in a user interface (230) to coder 10. Various functions are further provided along with the display in the user interface. For example, identified terms are presented with visual indicia (such as highlighting or coloring) to direct a coder's attention to the terms, and the terms may be selected, by for example clicking with a pointing device. Once a term is selected, the MDAE system invokes the healthcare organization coding system 12 (step 240), automatically providing to the healthcare organization coding system 12 coding relevant details. This allows coder 10 to avoid the otherwise necessary process steps of drilling down to a specific code from a number of high level general code descriptions. For example, in some cases, the information identified by the MDAE system, and provided to the healthcare organization coding system 12 upon selection of a term with in the MDAE's user interface, is sufficient for healthcare organization coding system 12 to directly identify a specific code. In other cases, however, there is still not enough information to identify a specific code, but there is enough information to identify general categories of relevant codes, and thus place coder 10 further down the coding hierarchy than she would otherwise be had she not had the MDAE system. Once the proper code is identified per step 240, this information is provided to the billing system 250, where bills are generated to be sent to payment organizations.

Figure 3:
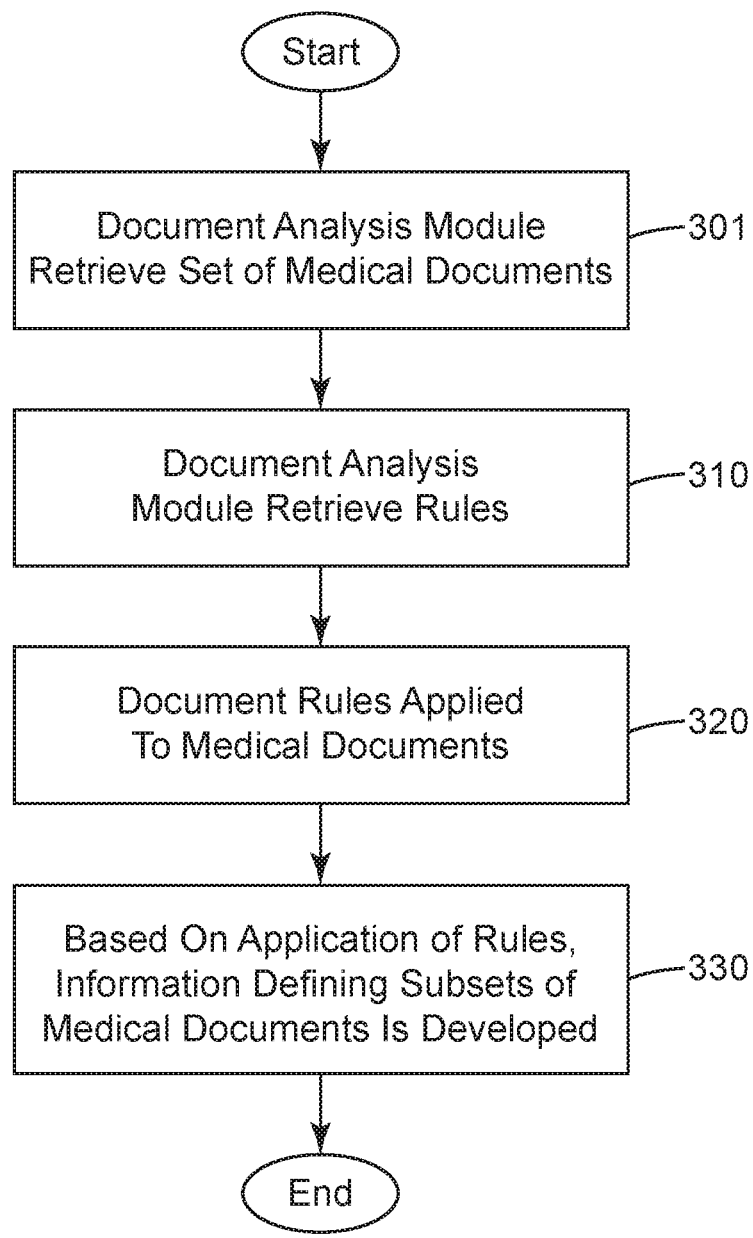
FIG. 3 is a high-level flowchart showing functionality of the MDAE system.
Figure 4:
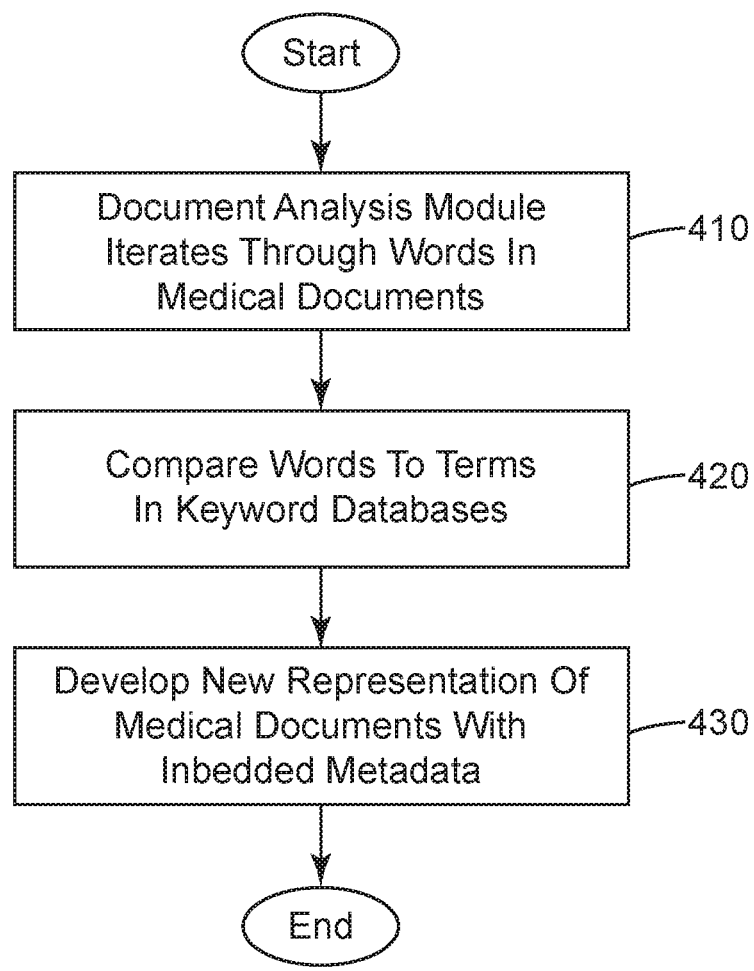
FIG. 4 is a high-level flowchart showing functionality of the MDAE system.

FIGS. 3 and 4 are flowcharts showing representative process steps involved in analyzing medical documentation 215. Per the architecture shown with respect to FIG. 1, these process steps would be facilitated by document analysis module 2. As earlier discussed, for a given set of documents associated with a patient encounter, document analysis module 2 has two objectives. The first objective is to identify subsets of the document relevant to coder 10. The second objective is to identify terms within the document that are relevant to coder 10, as well as associate various information relevant to interfacing, for particular terms, with the healthcare organization coding system 12. Though discussed in a particular sequence (objective 1 before objective 2), this is a design choice. In certain embodiments, objective 2 is first pursued, which then provides useful information for particular configurations of objective 1. For example, the fact of a high incidence of relevant terminology may mean that a particular subset of a document is identified. Alternatively, or in addition to, the healthcare organization may simply determine that particular documents, or particular subsections of documents, should always be displayed by user interface module 4. In such case, commensurate rules would be defined in MDEA rules database 7.

The process outlined in FIG. 3 starts with the document analysis module 2 retrieving a set of documents associated with a patient's encounter with a healthcare organization (301). These documents are, in one embodiment, already assembled in medical documentation database 6. Next, the document analysis module retrieves a set of rules from the MDAE rules database 7 (310). Next, the documents are iteratively examined by document analysis module 2, and the rules applied (320). Finally, based on the application of the rules, information defining subsets of medical documents is developed (330). This information may include, for example, references to sections of particular documents, or multiple sections of particular documents. This information is provided to MDAE module 3 for further processing.

The process outlined in FIG. 4 assumes the documents are already retrieved from the medical documents database 6 (as was done in the first step in the process outlined in FIG. 3). Document analysis module 2 then iterates through each word in each document (410) and compares these words to terms in keyword database 5. If a match is found, additional information is retrieved from keyword database 5 concerning the nature of the matched term. For example, it may be a term directly matched with a single ICD diagnosis code. Or, it could be a term that is suggestive of one of several particular ICD diagnosis codes. Or, it could be a term that suggests the exclusion of a particular one of several ICD diagnosis codes. Information concerning these matched terms are imbedded into a new representation of the document. This information might include a term type (for example, in the accompanying FIGs showing screen shots, several species of terms are represented. A first is a term associated with an ICD code. A second is a term indicative of a negation—that is, words that should signal that a particular aspect of a disease is not present. A third species is a term associated with demographic data useful for coding. An example of this third species would be the doctor's name. A fourth species is a term associated with a procedure. Other term species relevant to coding could be developed.

FIG. 5 is a rendering of a screen shot from MDAE system 1 as may be displayed to coder 10 via user interface module 4. In this rendering, document analysis module 2 has analyzed medical documents associated with a particular patient's encounter with a healthcare organization (as described above) and produced three medical document subsets (medical document subsets 510, 520, and 530). In this particular rendering, each of these document subsets is derived from a medical document. Rules in MDAE rules database 7 define the order of display of the document subsets, as well as the organization of the fields within each of the document subset sections.

The three document subsets 510, 520, and 530, include extracts from the medical documents on which they are based. Additionally, they may include field-type information to help organize portions of the medical documents. In the rendering of FIG. 5, visual indicia are associated with three separate species of terminology, per processes described above. The first terminology species associated with visual indicia in FIG. 5 is basic demographic data that is useful for coding. This includes the physician/surgeon name (field 540), as well as the discharge date (field 545). As can be seen, portions of the Discharge Summary view are field-based extracts (in other words, "Myron P. Gynesurg, MD" is pulled because it is associated with a particular field "PHYSICIAN/SURGEON"). The field shown in the Discharge Summary view may map to actual fields on the original discharge summary document (or documents), which makes extraction a straightforward task. In other embodiments, where sought after information is not necessarily associated with field name and is instead loosely formatted, rules can be employed to make good guesses on the constituents of sought after information.

The visual indicia associated with the terminology species may be associated with the typeset (for example, different fonts, different levels of bolding, underlying, italicizing, and so forth). Also, specific terms may be highlighted or outlined with a colored box, the box in one embodiment defining an area that may be selected by coder 10 via a pointing device such as a mouse. Upon selection by coder 10, a further user interface display may be presented having more information, discussed below. However, even without additional functionality available upon selecting a term, or the visual indicia associated with a term, highlighting terms relevant to demographics, diseases, and procedures may be helpful for coder 10.

The second species of medical terminology associated with visual indicia in FIG. 5 are those terms potentially relevant to an ICD-defined disease (including disease-relevant terms 550, 560, 570, and 572). These include in the discharge summary document subset 510, the terms "postmenopausal" (550), "bleeding" (560), and "hormonal replacement therapy" (570).

The third species of medical terminology associated with visual indicia in FIG. 5 are those terms potentially relevant to an ICD-defined procedure (including procedure-relevant terms 580 and 585), such as "total abdominal hysterectomy" (580) and "bilateral salpingo-oophorectomy" (585).

FIG. 6 is a rendering of a screen shot from MDAE system 1 as is displayed after coder 10 has selected visual indicia associated with disease-relevant term "leiomyoma" (572), from the screenshot rendering in FIG. 5. This rendering is termed the diagnosis view, because it shows up upon selection of visual indicia associated with a diagnosis. Upon selection of a term from FIG. 5, the selected term is used in search box 610, and medical documents associated with the patient's encounter with the healthcare organization are searched. Common variations of the term are also included in the search (for example, a search for leiomyoma includes words that include additional characters, such as leiomyomata). In one embodiment, all available text-based documents are searched. Portions of the medical documents that include term matches are displayed, with the search term highlighted in the results.

Figure 7:
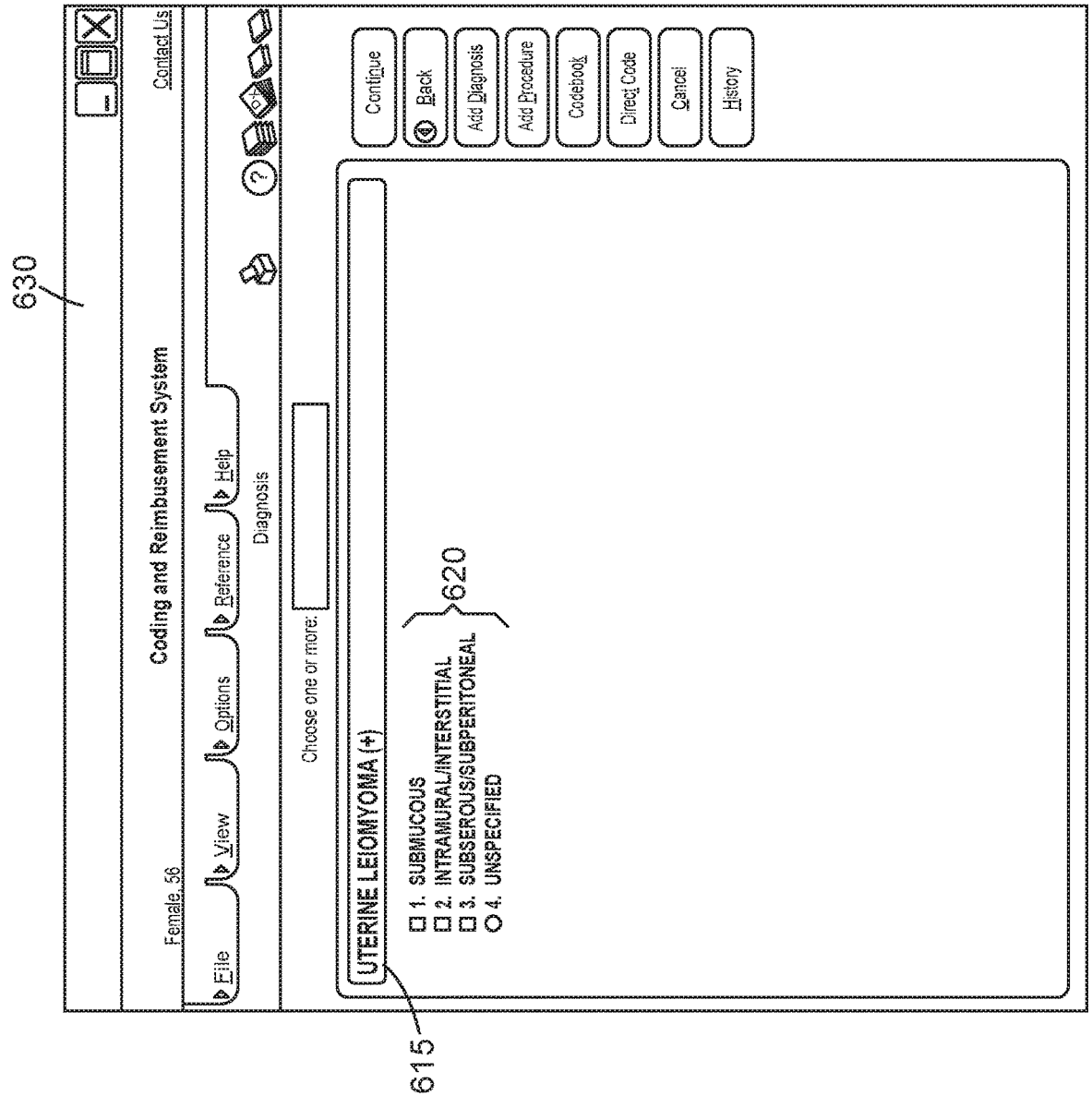
FIG. 7 is a screenshot from a user interface of the MDAE system.

FIG. 7 is a rendering of a screen shot from healthcare organization coding system 12. In this particular case, the screen shot is from commercially available "3M Coding and Reimbursement System" available from 3M HIS of Salt Lake City, Utah. Commensurate with the automatic search for a selected term described with respect to FIG. 6, information concerning the selected term is provided to the healthcare organization coding system 12. The particular information passed to healthcare organization coding system 12 may be tailored. In one embodiment, the MDAE system 1 has access to information concerning the disease and/or procedure hierarchy used by the healthcare organization coding system 12. In such case, MDAE system 1 may provide detailed information concerning where, in the healthcare organization coding system 12, coder 10 should be placed. On the other hand, in some embodiments, the selected term is provided to healthcare organization coding system 12, which in turn analyzes that term and determines on its own where in the coding process coder 10 should be placed. This latter approach treats the healthcare organization coding system 12 more akin to a black box. The passing of information between the MDAE system 1 and the healthcare organization coding system 12 may be accomplished in many ways. In one embodiment, a file is created by the MDAE system 1, which is then provided to the healthcare organization coding system 12. Other means of providing information between systems will be readily apparent to those skilled in the art.

Depending on the particular implementation details of the MDAE system and the healthcare organization coding system, different levels of information could be provided. For example, upon selection of particular terms, the MDAE system could provide additional terms that are known to be relevant to certain other aspects of the healthcare organization coding system. For example, in the example shown with respect to FIG. 5 and FIG. 7, FIG. 7 presents coder 10 with a screen soliciting input concerning species of uterine leiomyoma. If additional terms are present in the medical documents 6 that are suggestive of one of these, or suggestive of the exclusion of one of these, such information could be provided to healthcare organization coding system 12, and respective visual indicia associated with the suggested course (for example, if terms indicative of "submucous" are found to exist in the medical documentation, this term could be a special color, like green, whereas if terms are found suggesting the exclusion of intramural/interstitial, this term could be colored red, or even grayed out).

FIG. 8 is a rendering of the screen shot shown in FIG. 6, except that coder 10 has opted to search the medical documents for specific terms that the coder expects to be relevant to subsequent data entry in the healthcare organization coding system 12. For example, coder 10 may have seen the information presented in FIG. 7, and returned to the MDAE system to search for "submucous." Upon entering the characters, an alphabetized list of wildcard-type matches, along with the frequency of occurrence within the medical documentation, is displayed. As can be seen from the example, "submucosal" occurs three times, whereas subserosal occurs two times. This may indicate to coder 10 that each needs to be further investigated. If, however, submucosal occurred several times but subserous/subperitoneal occurred zero times, this may be enough for coder 10 to quickly conclude the uterine leiomyoma was of the submucous type.

Figure 9:
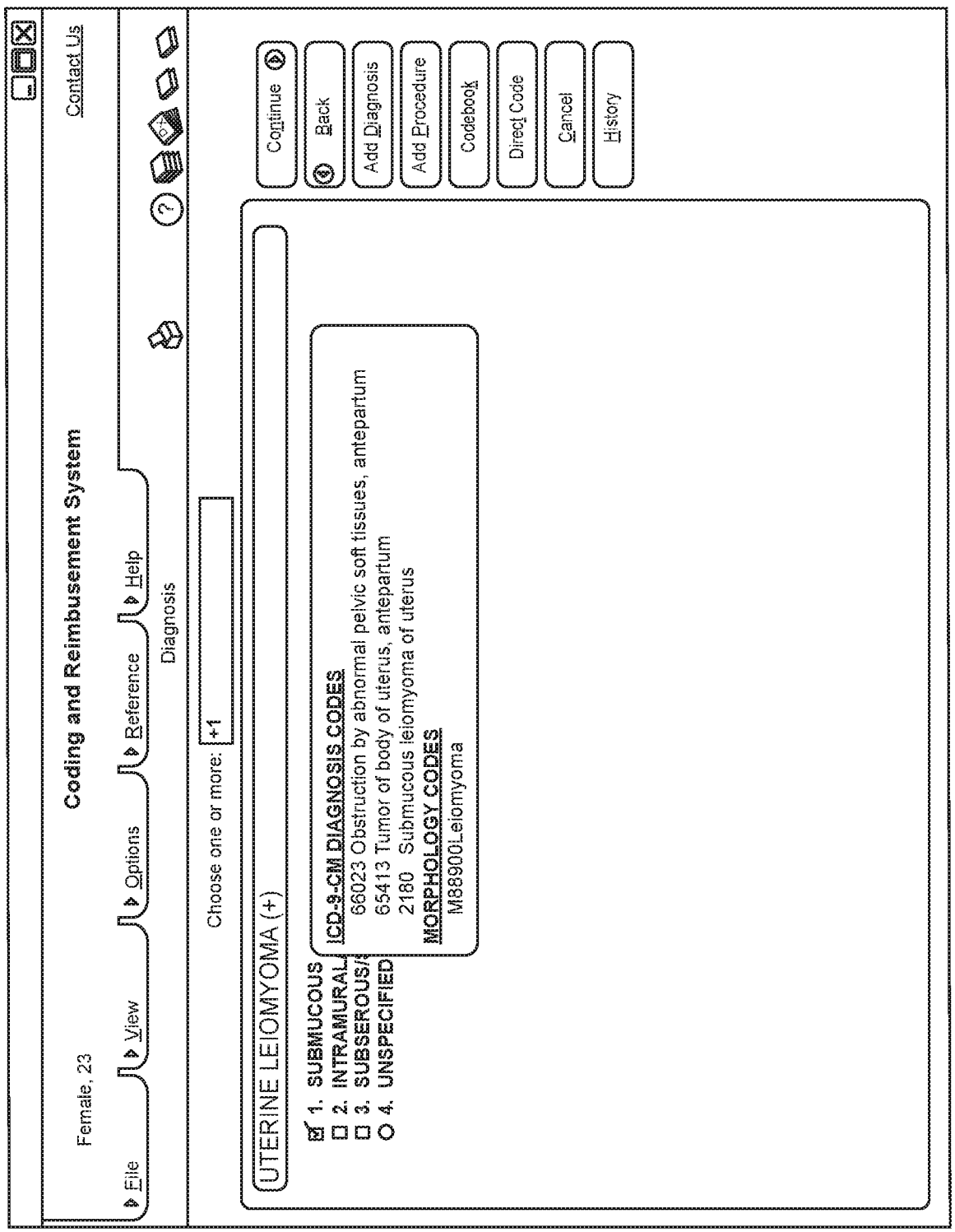
FIG. 9 is a screenshot from a user interface of the MDAE system.

FIG. 9 is a rendering of a screenshot of healthcare organization coding system 12 following coder 10's selection of "submucous." Specific ICD diagnosis codes are presented to coder 10, who may select a particular one. At this point, an ICD diagnosis code has been arrived at, and coder 10 can proceed with the next coding task.

Figure 10:
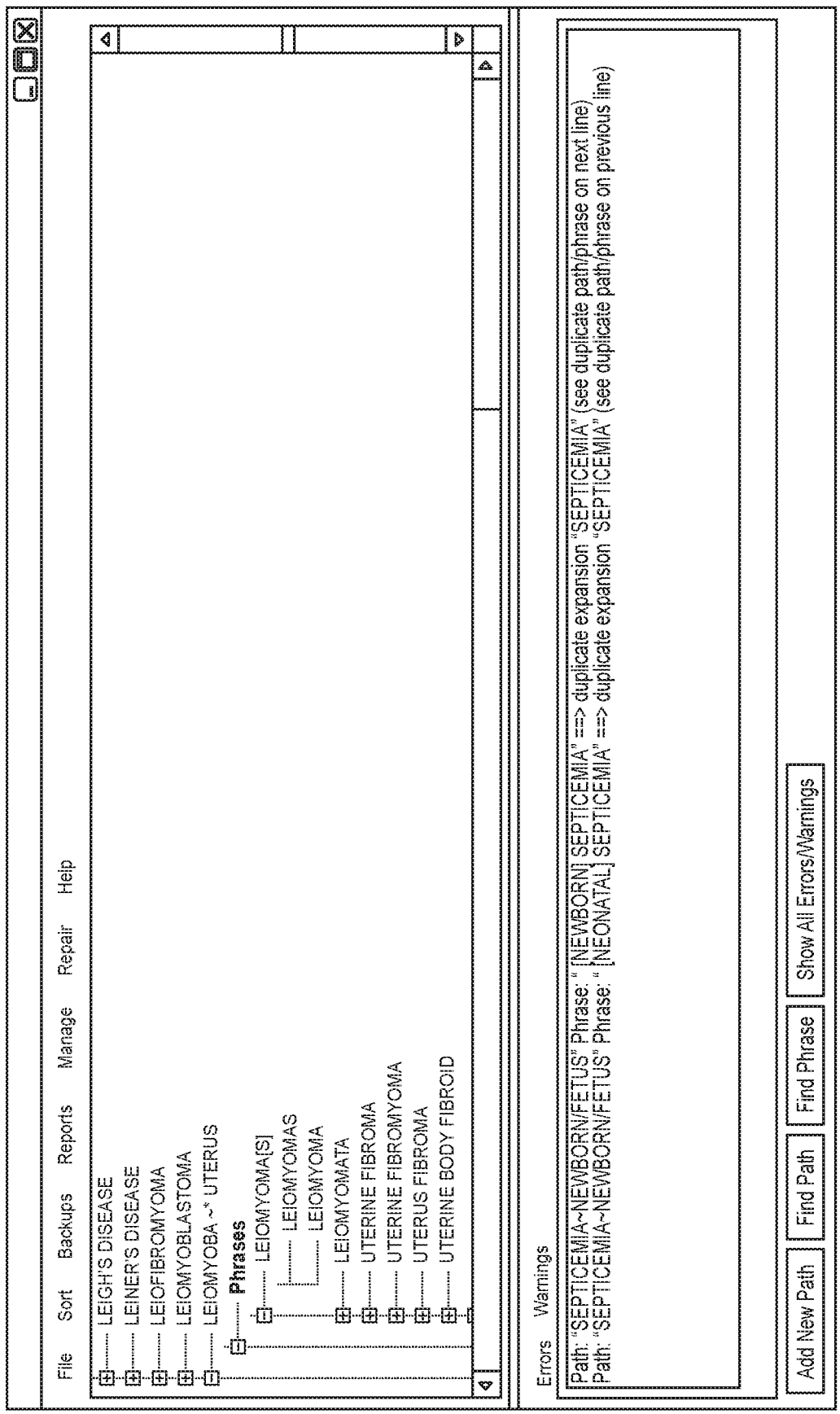
FIG. 10 is a screenshot from a utility that helps manage keywords.

FIG. 10 is a view of a tool used to manage keywords contained in keyword database 5. This tool allows management of relevant clinical terms used in the documentation extraction and analysis process. In the embodiment shown in FIG. 10, there is a tight integration between the keywords and the healthcare organization coding system—that is, the first order terms (such as LEIOMYOBA) may come directly from the healthcare organization coding system, then variations on the term are identified under "PHRASES."

Many modifications and other embodiments of the invention will come to mind to one skilled in the art to which this invention pertains, having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method comprising:
    obtaining, by a processor of a computing device and from one or more electronic document databases, a plurality of uncoded electronic documents associated with a patient's encounter with a health care organization;
    obtaining, by the processor and from a rules database, a set of rules defining, for given types of electronic documents, a plurality of terms relevant to medical coding of the plurality of uncoded electronic documents, wherein the set of rules comprise a relevance score indicative of a relevance of respective terms of the plurality of terms to medical coding;
    generating, by the processor, subsets of the plurality of uncoded electronic documents by applying the set of rules to the plurality of electronic documents, wherein:
        each of the subsets comprises a respective extract from the plurality of uncoded electronic documents comprising one or more terms of the plurality of terms defined by the set of rules as being relevant to medical coding;
        the subsets comprise a first portion of the plurality of uncoded electronic documents comprising at least some terms of the plurality of terms, the first portion being different than a second portion of the plurality of electronic documents that does not comprise any terms of the plurality of terms;
        generating the subsets by applying the set of rules comprises selecting the subsets of the plurality of uncoded electronic documents that include terms with respective relevance scores indicative of greater relevance to medical coding than terms of other subsets of the second portion of the plurality of uncoded electronic documents; and
    generating, for display, a user interface comprising a display area comprising at least one subset of the subsets of the plurality of uncoded electronic documents that include at least some of the first portion of the electronic documents instead of the second portion of the electronic documents;
    generating, for display in the display area, visual indicia identifying the one or more terms of the plurality of terms defined by the rules as being relevant to medical coding from the at least one subset of the subsets of the plurality of uncoded electronic documents that include at least some of the first portion of the electronic documents;
    receiving, via the user interface, a selection of one of a term of the one or more terms of the plurality of terms defined by the rules as being relevant to medical coding or the visual indicia identifying the term;
    responsive to receiving the selection, determining at least a portion of a medical code related to the term of the selection; and
    generating, for display as part of the user interface, at least the portion of the medical code related to the term of the selection.

2. The computer-implemented method of claim 1, wherein the set of rules take into consideration occurrences of the one or more terms of the plurality of terms within the plurality of uncoded electronic documents, the one or more terms being received from the terms database.

3. The computer-implemented method of claim 2, wherein the one or more terms are associated with particular codes that may be associated with the patient or the patient's encounter with the healthcare organization.

4. The computer-implemented method of claim 1, wherein the particular codes are International Classification of Diseases (ICD)-based codes.

5. The computer-implemented method of claim 1, wherein taking into consideration the occurrence of the one or more terms comprises determining the frequency of the one or more terms within portions of a given electronic document.

6. The computer-implemented method of claim 1, wherein the visual indicia comprise a visual effect comprising at least one of highlighting, underlining, font, font size, underlining, and italicizing.

7. The computer-implemented method of claim 6, further comprising, responsive to receiving the selection, generating, for display as part of the user interface, one or more portions of the electronic document that includes the term of the selection.

8. A non-transitory computer-readable medium comprising instructions that, when executed, cause a processor of a computer to:
    obtain, from one or more electronic document databases, a plurality of uncoded electronic documents associated with a patient's encounter with a health care organization;
    obtain, from a rules database, a set of rules defining, for given types of electronic documents, a plurality of terms relevant to medical coding of the plurality of uncoded electronic documents, wherein the set of rules comprise a relevance score indicative of a relevance of respective terms of the plurality of terms to medical coding;
    generate subsets of the plurality of uncoded electronic documents by applying the set of rules to the plurality of electronic documents, wherein:
        each subset comprises a respective extract from the plurality of uncoded electronic documents comprising one or more terms of the plurality of terms defined by the set of rules as being relevant to medical coding;

the subsets comprise a first portion of the plurality of uncoded electronic documents comprising at least some terms of the plurality of terms, the first portion being different than a second portion of the plurality of electronic documents that does not comprise any terms of the plurality of terms;

generating the subsets by applying the set of rules comprises selecting the subsets of the plurality of uncoded electronic documents that include terms with respective relevance scores indicative of greater relevance to medical coding than terms of other subsets of the second portion of the plurality of uncoded electronic documents; and generate, for display, a user interface comprising a display area comprising at least one subset of the subsets of the plurality of uncoded electronic documents that include at least some of the first portion of the electronic documents instead of the second portion of the electronic documents;

generate, for display in the display area, visual indicia identifying the one or more terms of the plurality of terms defined by the rules as being relevant to medical coding from the at least one subset of the subsets of the plurality of uncoded electronic documents that include at least some of the first portion of the electronic documents;

receive, via the user interface, a selection of one of a term of the one or more terms of the plurality of terms defined by the rules as being relevant to medical coding or the visual indicia identifying the term;

responsive to receiving the selection, determine at least a portion of a medical code related to the term of the selection; and generate, for display as part of the user interface, at least the portion of the medical code related to the term of the selection.

9. The non-transitory computer-readable medium of claim 8, wherein the set of rules take into consideration the occurrences of the one or more terms of the plurality of terms within the plurality of uncoded electronic documents, the one or more terms being received from the terms database.

10. The non-transitory computer-readable medium of claim 9, wherein the one or more terms are associated with particular codes that may be associated with the patient or the patient's encounter with the healthcare organization.

11. The non-transitory computer-readable medium of claim 8, wherein the particular codes are International Classification of Diseases (ICD)-based codes.

12. The non-transitory computer-readable medium of claim 8, wherein taking into consideration the occurrence of the one or more terms comprises determining the frequency of the one or more terms within portions of a given electronic document.

13. The non-transitory computer-readable medium of claim 8, wherein the visual indicia comprise a visual effect comprising at least one of highlighting, underlining, font, font size, underlining, and italicizing.

14. The non-transitory computer-readable medium of claim 8, further comprising instructions that cause the processor to, responsive to receiving the selection, generate, for display as part of the user interface, one or more portions of the electronic document that includes the term of the selection.

15. A system comprising:
one or more microprocessors and memory which executes software to cause the system to:

obtain, from one or more electronic document databases, a plurality of uncoded electronic documents associated with a patient's encounter with a health care organization;

obtain, from a rules database, a set of rules defining, for given types of electronic documents, a plurality of terms relevant to medical coding of the plurality of uncoded electronic documents, wherein the set of rules comprise a relevance score indicative of a relevance of respective terms of the plurality of terms to medical coding;

generate subsets of the plurality of uncoded electronic documents by applying the set of rules to the plurality of electronic documents, wherein:

each subset comprises a respective extract from the plurality of uncoded electronic documents comprising one or more terms of the plurality of terms defined by the set of rules as being relevant to medical coding;

the subsets comprise a first portion of the plurality of uncoded electronic documents comprising at least some terms of the plurality of terms, the first portion being different than a second portion of the plurality of electronic documents that does not comprise any terms of the plurality of terms;

generating the subsets by applying the set of rules comprises selecting the subsets of the plurality of uncoded electronic documents that include terms with respective relevance scores indicative of greater relevance to medical coding than terms of other subsets of the second portion of the plurality of uncoded electronic documents; and generate, for display, a user interface comprising a display area comprising at least one subset of the subsets of the plurality of uncoded electronic documents that include at least some of the first portion of the electronic documents instead of the second portion of the electronic documents;

generate, for display in the display area, visual indicia identifying the one or more terms of the plurality of terms defined by the rules as being relevant to medical coding from the at least one subset of the subsets of the plurality of uncoded electronic documents that include at least some of the first portion of the electronic documents;

receive, via the user interface, a selection of one of a term of the one or more terms of the plurality of terms defined by the rules as being relevant to medical coding or the visual indicia identifying the term;

responsive to receiving the selection, determine at least a portion of a medical code related to the term of the selection; and generate, for display as part of the user interface, at least the portion of the medical code related to the term of the selection.

16. The system of claim 15, wherein the set of rules take into consideration the occurrences of the one or more of the plurality of terms within the plurality of uncoded electronic documents, the one or more terms being received from the terms database.

17. The system of claim 16, wherein the one or more terms have been previously associated with particular codes that may be associated with the patient or the patient's encounter with the healthcare organization.

18. The system of claim 15, wherein the particular codes are International Classification of Diseases (ICD)-based codes.

19. The system of claim 15, wherein taking into consideration the occurrence of the one or more terms comprises determining the frequency of the one or more terms within portions of a given electronic document.

20. The system of claim 15, wherein the visual indicia comprise a visual effect comprising at least one of highlighting, underlining, font, font size, underlining, and italicizing.

21. The system of claim 15, wherein the one or more microprocessors and memory executes software to cause the system to, responsive to receiving the selection, generate, for display as part of the user interface, one or more portions of the electronic document that includes the term of the selection.

22. The computer-implemented method of claim 1, wherein determining the at least the portion of the medical code comprises determining the at least the portion of the medical code comprises determining a list of a plurality of International Classification of Diseases (ICD)-based codes associated with the term for selection of a particular one ICD-based code of the plurality of ICD-based codes.

* * * * *